United States Patent
Cefai et al.

(10) Patent No.: US 8,729,912 B2
(45) Date of Patent: May 20, 2014

(54) DISPLACEMENT SENSOR

(75) Inventors: Joseph John Cefai, Swansea (GB); Julian Shapley, Cardiff (GB); Neil Thomas, Swansea (GB); Matthew Powell, Ebbw Vale (GB); Mark Stephen Jones, Swansea (GB)

(73) Assignee: Cellnovo Limited, Swansea (GB)

( * ) Notice: Subject to any disclaimer, the term of this patent is extended or adjusted under 35 U.S.C. 154(b) by 359 days.

(21) Appl. No.: 13/075,796

(22) Filed: Mar. 30, 2011

(65) Prior Publication Data
US 2011/0316562 A1    Dec. 29, 2011

Related U.S. Application Data

(63) Continuation of application No. PCT/GB2009/002353, filed on Oct. 2, 2009.

(51) Int. Cl.
*G01R 27/26* (2006.01)
(52) U.S. Cl.
USPC .............................. 324/662; 324/663
(58) Field of Classification Search
USPC .................................. 324/662, 663
See application file for complete search history.

(56) References Cited

U.S. PATENT DOCUMENTS

| | | | |
|---|---|---|---|
| 4,206,401 A | 6/1980 | Meyer | |
| 4,587,850 A | 5/1986 | Moser | |
| 4,961,055 A * | 10/1990 | Habib et al. | 324/662 |
| 5,585,733 A | 12/1996 | Paglione | |
| 2006/0192569 A1 | 8/2006 | Hetherington et al. | |
| 2008/0173073 A1 * | 7/2008 | Downie et al. | 73/49.8 |

FOREIGN PATENT DOCUMENTS

| | | |
|---|---|---|
| DE | 4306061 A1 | 9/1994 |
| DE | 10313327 A1 | 10/2004 |
| GB | 307620 | 3/1929 |
| GB | 2400158 A | 6/2004 |
| GB | 2400158 B | 3/2006 |
| GB | 2443260 A | 4/2008 |
| JP | 2003154190 A | 5/2003 |
| WO | 2004088148 A1 | 10/2004 |

OTHER PUBLICATIONS

UK Search Report for Application No. GB0818077.0 dated Oct. 22, 2008.

* cited by examiner

*Primary Examiner* — Amy He
(74) *Attorney, Agent, or Firm* — Roy P. Issac, Esq.; Carolyn S. Elmore, Esq.; Elmore Patent Law Group, P.C.

(57) ABSTRACT

A linear capacitance displacement transducer (1) comprising first (2) and second (3) fixed capacitor plate and a dielectric structure (5) moveable longitudinally within a space (4) between the first (2) and second (3) capacitor plates, the dielectric structure (5) being operatively coupled to a moveable element (8). The capacitor plates and the dielectric material may be cylindrical and disposed coaxially and concentrically. The transducer (1) enables a displacement sensor that is capable of monitoring liquid levels in a syringe type drug reservoir (101) with sufficient sensitivity as to allow detection of erroneous drug delivery. The sensor is inexpensive to manufacture and provides reliable performance through robust design.

41 Claims, 3 Drawing Sheets

DISPLACEMENT SENSOR

RELATED APPLICATION

This application is a continuation of International Application No. PCT/GB2009/002353, which designated the United States and was filed on Oct. 2, 2009, which claims priority under 35 U.S.C. §119 or 365 to United Kingdom Application No. 0818077.0, filed on Oct. 2, 2008. The entire teachings of the above applications are incorporated herein by reference.

FIELD OF THE INVENTION

In devices for the programmed delivery of therapeutic products into the human or animal body, there is generally provided a pressurised reservoir of therapeutic product working in cooperation with a pumping chamber and valve means. The therapeutic product is typically pumped by the device through a tube to a cannula that pierces the patient's skin. The device can be capable of providing a variable rate of infusion of the therapeutic product to the patient over several days. This invention is directed to an improved displacement sensor for the pressurised reservoir.

BACKGROUND TO THE INVENTION

Many different measurement techniques have been used previously as the basis for displacement sensors.

In one type of displacement sensor the action of linearly or rotationally displacing a wiper of a potentiometer is converted to a voltage and/or current signal. Such potentiometric sensors often suffer from the problems of mechanical wear, frictional resistance in the wiper action, limited resolution in wire-wound units, and high electronic noise.

Linear Variable Displacement Transducers (LVDT) are commonly available. An LVDT typically includes three coils of wire wound on a hollow form. A core of permeable material can slide freely through the centre of the form. The inner, primary coil is excited by an ac source. Flux formed by the primary coil is linked to two outer, secondary coils, inducing an ac voltage in each coil depending on the position of the core. If the two secondary coils are wired in series opposition then the two voltages will subtract; that is, a differential voltage is formed. When the core is centrally located, the net voltage is zero. When the core is moved to one side, the net voltage amplitude will increase. In addition, there is a change in phase with respect to the source when the core is moved to one side or the other. Additionally, these devices require separate coils at either end of the measurement coils to provide electrical shielding to create a low noise transducer. These manufacturing requirements make these transducers expensive to manufacture and have a length dimension at least twice the distance they can measure.

A number of devices have also been described based on optical measurement systems such as optical encoders. Devices based on ultrasonic techniques have also been described. These devices tend to be expensive to manufacture and are restricted in the type of application in which they can be employed.

A variety of capacitance based displacement sensors have been described for measuring or detecting linear displacements. One type of capacitance displacement sensor is based on the principle of two opposing plates, where measurement of displacement either alters the overlapping area of the two plates or changes the dielectric properties of the gap between the plates. Examples of this type of displacement sensor are offered below.

GB 1275060 A discloses a displacement sensor comprising of guided rod forming a first plate of the capacitor and a receptor tube in which the rod moves in and out forming a second pate of the capacitor.

U.S. Pat. No. 4,961,055 discloses a displacement sensor similar to that of GB 1275060 A and further discloses a third tube that acts to shield the sensing plate of the capacitor from electrostatic charges, which can cause signal noise.

A number of other moving plate capacitor sensors have also been described that utilise patterns of electrodes on either flat or tubular plates. Examples of these are given by JP 8-159704 and GB 2273567 A. The construction of these devices also presents considerable challenges in manufacturing inexpensive devices.

The use of capacitance displacement sensors has been described for a variety of applications including monitoring fluid levels in reservoirs, as disclosed in EP 0520201 A.

U.S. Pat. No. 5,135,485 discloses a capacitance measurement employed in a drug reservoir to either detect when the reservoir is empty or provide a measure of the level of liquid in the reservoir. The sensor described for monitoring the level of liquid in the reservoir comprises two plates of a capacitor with the liquid forming the dielectric between them. The greater the quantity of liquid present in the reservoir the more the gap between the plates becomes filled with the liquid and this is reflected in the capacitance measured by the sensor.

U.S. Pat. No. 6,210,368 discloses a capacitor based sensor that monitors liquid levels in a reservoir. In one embodiment an amount of overlap between two plates of a capacitor changes as the reservoir volume changes. In another embodiment an amount of liquid phase propellant absorbed in a dielectric material of a capacitor changes according to the reservoir volume, causing a change in the dielectric properties of the capacitor.

U.S. Pat. No. 6,352,523 discloses a method for measuring the amount of insulin remaining in a syringe after an administration based on a barrel and plunger of a syringe being adapted as the two plates of a coaxial capacitor. The device additionally requires that the syringe is placed into a reader to generate the displacement information.

Alternative techniques for monitoring levels of a drug in a reservoir include the use of optical encoders. U.S. Pat. No. 4,498,843 and WO2004/009163 both describe a linear displacement measurement system based on an optical encoder that is used to monitor the position of a syringe barrel as part of an infusion system.

There is a need in the art for a displacement sensor capable of monitoring the level of liquid in a syringe type drug reservoir with sufficient sensitivity as to allow detection of erroneous drug delivery. It is also required that the sensor is inexpensive to manufacture and provides reliable performance through robust design.

SUMMARY OF THE INVENTION

According to a first aspect of the present invention there is provided a linear capacitance displacement transducer comprising a first cylindrical capacitor plate, a second cylindrical capacitor plate disposed around the first cylindrical capacitor plate so as to form a space between the first and second cylindrical capacitor plates, the first and second cylindrical capacitor plates being substantially spatially fixed relative to one another, and a third cylinder composed of dielectric material moveable longitudinally within the space such that a proportion of said space filled with the dielectric material can be altered relative to a fixed electric field created, in use, between the first and second cylindrical capacitor plates.

According to a second aspect of the present invention there is provided a reservoir for containing a volume of fluid bound in part by an moveable element, in combination with a linear capacitance displacement transducer for measuring the volume of fluid contained in the reservoir, the displacement transducer comprising a fixed structure including first and second capacitor plates, and a dielectric structure moveable longitudinally within a space between the first and second capacitor plates, wherein the moveable dielectric structure is operatively coupled to the moveable element.

According to a third aspect of the present invention there is provided an infusion system for infusion of liquid therapeutic product, including a linear capacitance displacement transducer according to the first aspect, or a linear capacitance displacement transducer in combination with a reservoir according to the second aspect.

In the linear capacitance displacement transducer the electric field created, in use, between the first and second capacitor plates remains stationary whilst the proportion of the space between these plates that is filled with high dielectric material is altered by movement of the dielectric structure. This construction is advantageous in that since the first and second capacitor plates are substantially spatially fixed relative to one another, electrical connections for connecting thereto do not need to move thereby simplifying and making more robust the transducer and improving the reliability of a signal output by the transducer. Additionally, since the second capacitor plate is substantially spatially fixed relative to the electric field created, in use, the second plate acts as an effective shield against adverse external electrical influences.

In a preferred embodiment of the invention, the fixed structure of the linear capacitance displacement transducer is a durable portion, whereas the reservoir and the moveable structure of the linear displacement transducer are a disposable portion, of an infusion system. In this manner, a disposable reservoir initially containing liquid therapeutic product may be formed integrally with the dielectric portion of the transducer to be fitted onto the durable portion of the infusion system having the electrical portion of the transducer. This allows a highly accurate transducer measurement to be made whilst keeping the manufacturing cost of the disposable portion of the infusion system low.

BRIEF DESCRIPTION OF THE DRAWINGS

Examples of the present invention will now be described in detail with reference to the accompanying drawings, in which.

DETAILED DESCRIPTION

Figure 1:
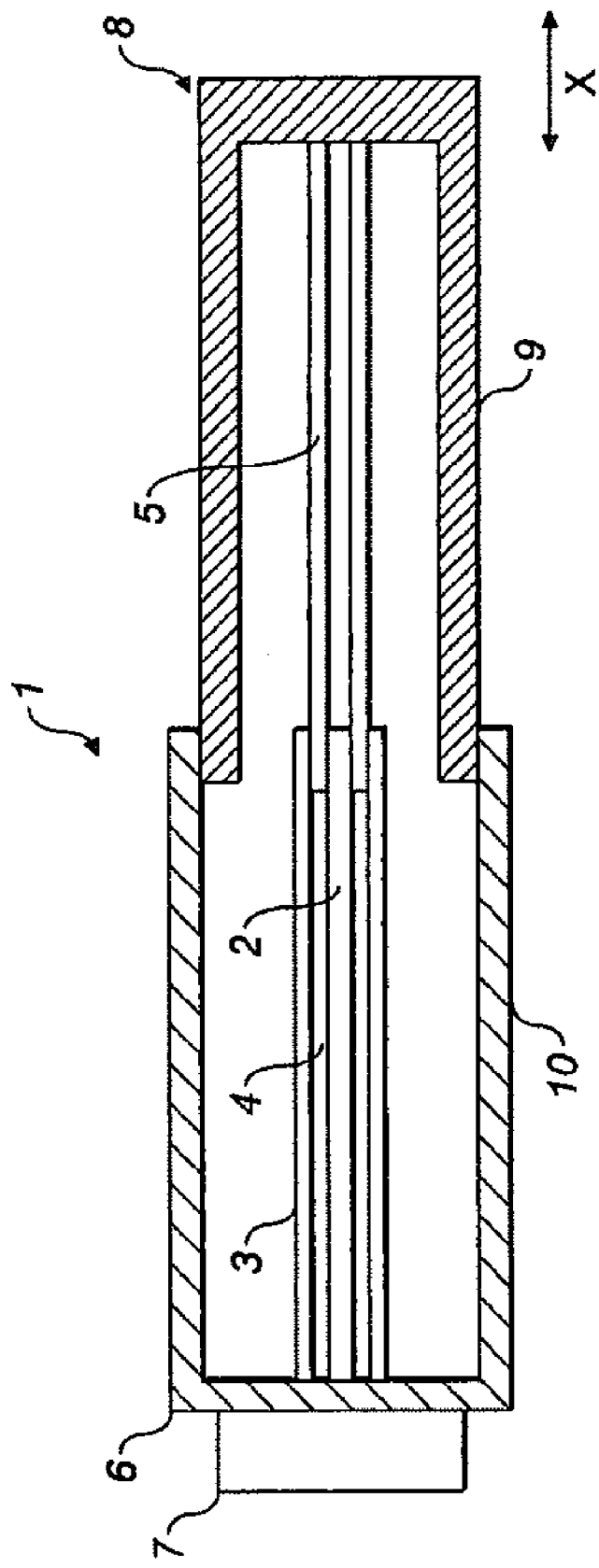
FIG. 1 is a schematic view of an embodiment of the linear capacitance displacement transducer in accordance with the invention, shown in an extended position.

Turning firstly to FIG. 1, the linear capacitance displacement transducer 1 includes a first capacitor plate 2 and a second capacitor plate 3 defining a space 4 between the first and second capacitor plates 2,3. The displacement transducer 1 further includes a dielectric structure 5 movable longitudinally within the space 4 in the direction of arrows X. The first and second capacitor plates 2,3 are electrically and physically connected to a printed circuit board or similar layer 6 having a semiconductor integrated circuit 7, such as AD7746, mounted thereon. The dielectric structure 5 is operatively coupled to a movable element 8. The movable element 8 is connected to guide means 9 cooperating with guide means 10 extending from the printed circuit board 6.

In the preferred embodiment shown in FIG. 1 the first capacitor plate 2 is a solid right circular cylinder disposed coaxially and concentrically with a hollow right circular cylinder of the second capacitor plate 3. It will be appreciated by those skilled in the art that the first and second capacitor plates 2,3 need not necessarily be cylinders but may instead be flat plates, for example. Cylindrical capacitor plates are preferred as the outer, second cylindrical capacitor plate 3 effectively shields the fixed electric field created, in use, between the first and second cylindrical capacitor plates 2,3. It will also be appreciated by those skilled in the art that the first and second capacitor plates 2,3 need not be right circular cylinders and may instead take solid or hollow hexagonal, octagonal or other polygonal or irregular forms. The first and second cylinders 2,3 need not be disposed concentrically but it is preferred that they are so such that the electric field created is substantially uniform within a cross-section of the transducer 1.

In the preferred embodiment shown in FIG. 1, the first and second capacitor plates 2,3 are of substantially the same length. However, it is envisaged that in alternative embodiments, the first and second capacitor plates 2,3 may be of different lengths and in particular the second cylinder 3 may be longer than the first cylinder 1 to provide more effective shielding against electrostatic interference.

The guide means 10 may have a further function as a fourth cylinder disposed around the second cylindrical capacitor plate 3 for providing additional shielding against electrostatic interference to further improve the signal quality of the transducer 1.

The first and second capacitor plates 2,3 are physically connected to the printed circuit board 6 which acts as a support structure for supporting adjacent ends of the first and second capacitor plates 2,3. It will be appreciate by those skilled in the art that a support structure other than the printed circuit board 6 may be provided as the physical connection at those ends of the first and second capacitor plates 2,3, and wiring may be provided to a separate printed circuit board. However, to achieve space saving and drive down manufacturing costs the printed circuit board 6 acts as the physical support structure for the first and second capacitor plates 2,3.

The first and second capacitor plates 2,3 are electrically isolated and connected to the printed circuit board having the integrated circuit 7 for performing conversion of a capacitance signal output by the first and second capacitor plates 2,3. Integrated circuit 7 also performs analog to digital conversion of the raw capacitance signal output by the first and second capacitor plates 2,3. The AD7746 integrated circuit is provided as a purely exemplary integrated circuit and it will be appreciated by those skilled in the art that other circuits may be used in the alternative.

To increase the effective surface area of the capacitor plates 2,3, these may have a fluted surface. To ensure that the dielectric structure 5 is reliably retained between the first and second capacitor plates 2,3 the dielectric structure 5 may also be provided with a fluted surface. It is intended that the dielectric structure is slidably movable within the space 4 by a clearance fit with the capacitor plates 2,3 but leaving little, if any, play.

In some preferred applications, the dielectric structure may be biased into or from the space 4 in the longitudinal direction. The bias may be provided by a spring or other such means and is particularly suitable where the movable member 8 connected to the distal end of the dielectric structure 5 constitutes a part of a reservoir or the like, a plunger of which is displaced and the transducer 1 measures that displacement.

Figure 2:
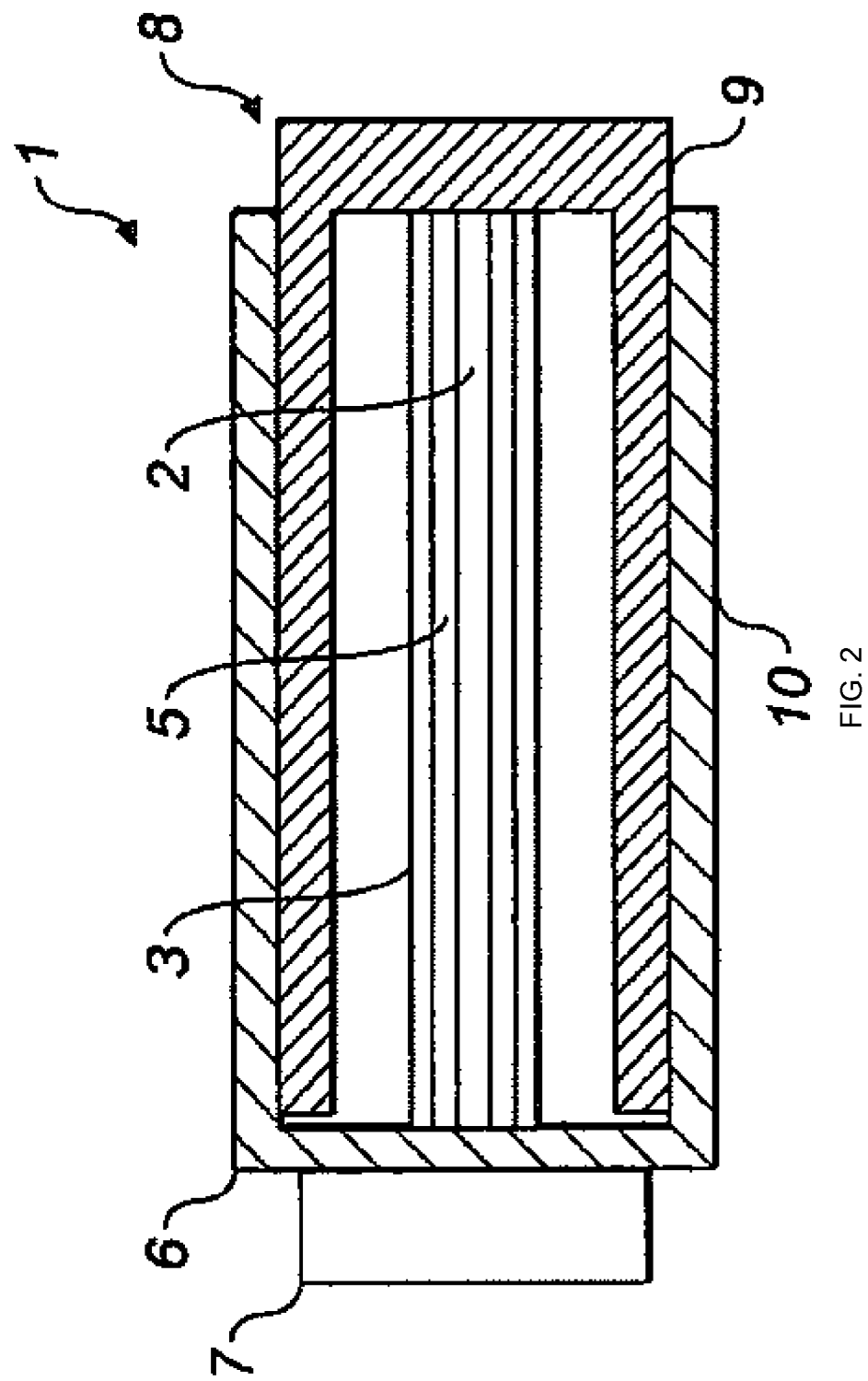
FIG. 2 is a schematic view of the transducer of FIG. 1, shown in a retracted position.

The linear capacitance displacement transducer 1 is shown in a retracted position in FIG. 2 in which the dielectric structure 5 occupies substantially all of the space 4 between the first and second capacitor plates 2,3. As the dielectric structure 5 moves between the fully extended and retracted positions of FIGS. 1 and 2, respectively, the proportion of the space 4 between the first and second capacitor plates 2,3 that is filled with the dielectric material 5 changes between a minimum and a maximum. The capacitance signal output by these first and second capacitor plates 2,3 can be calibrated to the linear displacement of the movable member 8 according to the change in capacitance as the movable element 8 moves between the fully extended and fully retracted positions. In this manner, the position and relative displacement of the movable element 8 can be measured by interrogating the capacitance signal.

The linear capacitance displacement transducer 1 of the invention has broad application to a variety of devices. This may include displacement of a piston within its cylinder, displacement of a bowden cable, displacement of a linear switch, and the like. Its application is almost boundless and many other uses will be readily appreciated by those skilled in the art.

However, a particular application of the linear capacitance displacement transducer in accordance with the invention is in combination with a reservoir for containing a volume of fluid bound in part by a movable element, such as a plunger. The plunger may be, or may be attached to, the movable element 8 described with reference to the linear capacitor displacement transducer 1 of FIGS. 1 and 2.

The reservoir and transducer 1 in combination may form a fixed structure including the first and second capacitor plates 2,3, and the dielectric structure 5 movable longitudinally within the space 4 between the first and second capacitor plates 2,3. The movable dielectric structure 5 is operatively coupled to the movable element 8 as described previously. The fixed structure of the transducer may form a durable part, and the reservoir and the movable structure of the transducer may form a disposable part, with the movable element of the reservoir being integrally formed with the movable structure. Such a combination is particularly suitable for use in an infusion system for infusion of liquid therapeutic product.

Figure 3:
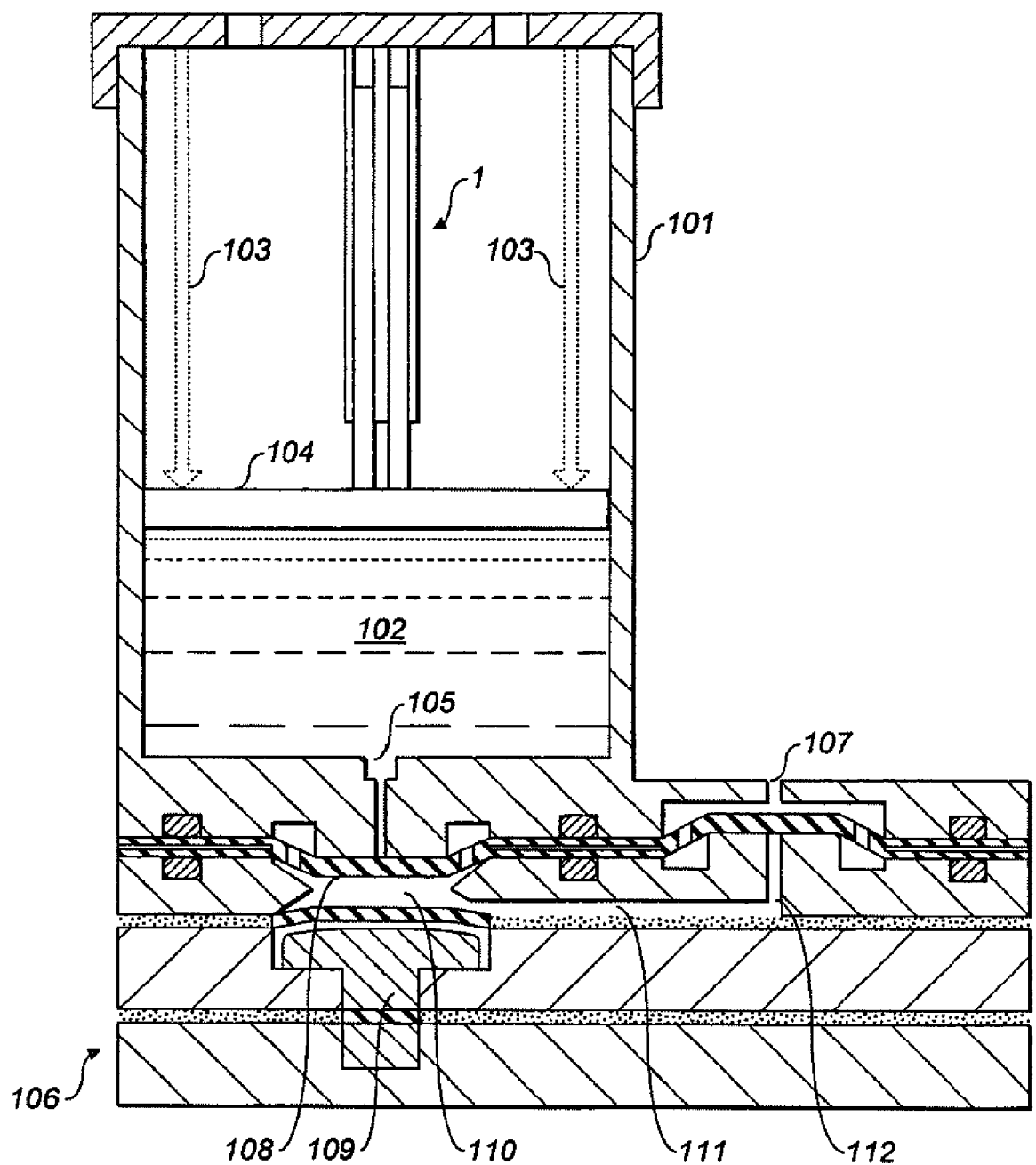
FIG. 3 is a schematic view of an infusion system comprising a reservoir and a transducer in accordance with an embodiment of the invention.

The infusion system shown in FIG. 3 includes a pressurised reservoir 101 of therapeutic product 102. The therapeutic product 102 is pressurised within the reservoir by application of a force, indicated by 103, on a plunger 104 movable within the reservoir cavity. An outlet 105 of the reservoir is connected to an inlet of a micropump 106. Means for fluidically coupling the micropump 106 to a human or animal body to which the therapeutic product is to be delivered is connected at one end to a patient, and at the other end to an outlet 107 of the micropump 106. This means may be a cannular or other similar device.

In the micropump 106, the fluid inlet 105 leads to an inlet valve 108. Operation of an actuator 109 having a gearing assembly causes a change in volume of a pumping chamber 110. Upon increasing the volume of the pumping chamber 110 by operation of the geared actuator 109 the inlet valve 105 opens and fluid flows from the inlet 105 through the inlet valve 108 to fill the pumping chamber 110. Once the pumping chamber 110 is full, operation of the geared actuator 109 to produce the volume of the pumping chamber 110 forces the fluid along a conduit 111 to an outlet valve 112. Since the fluid passing through the conduit 111 is under pressure from the geared actuator 109, the outlet valve 112 opens and fluid exits the pump 106 via outlet 107.

The inlet and outlet valves 108,112 are one way valves such as described in the applicant's co-pending UK patent application GB 0621343.3, the contents of which are incorporated herein by reference. The actuator, which may be a geared actuator 109, such as described in applicant's co-pending UK patent application GB0621344.1, the contents of which is incorporated herein by reference.

The one way valves 108,112 are such that upon a decrease in the volume of the pumping chamber 110 fluid therein does not pass through the inlet valve 108 to the inlet 105 and only passes along the conduit 111. Also, the outlet valve 112 closes when the pressure in the fluid in the conduit 111 decreases below a predetermined value. Repeated operation of the geared actuator 109 causes fluid to be pumped from the inlet 105 to the outlet 107.

The actuator 109 is preferably controlled by an electronics module (not shown) that works in cooperation with at least one flow rate indicator to ensure programmed delivery of the therapeutic product with a high degree of accuracy. The at least one flow rate indicator may be derived from an output of the linear capacitance displacement transducer 1 of the present invention.

Various modifications of the invention are envisaged as will be appreciate by the skilled person without departing from the scope of the invention, which is defined by the appended claims.

The invention claimed is:

1. A linear capacitance displacement transducer comprising:
   a first cylindrical capacitor plate;
   a second cylindrical capacitor plate disposed around the first cylindrical capacitor plate so as to form a space between the first and second cylindrical capacitor plates, the first and second cylindrical capacitor plates being substantially spatially fixed relative to one another; and
   a third cylinder composed of dielectric material moveable longitudinally within said space such that a proportion of said space filled with the dielectric material can be altered relative to a fixed electric field created, in use, between said first and second cylindrical capacitor plates,
   wherein said first and second capacitor plates are electrically connected to a circuit board and wherein said first and second capacitor plates are physically connected to said circuit board such that said circuit board acts as a support structure for supporting adjacent ends of said first and second capacitor plates.

2. A linear capacitance displacement transducer according to claim 1, wherein the cylinders are disposed coaxially.

3. A linear capacitance displacement transducer according to claim 1, wherein the cylinders are right circular cylinders.

4. A linear capacitance displacement transducer according to claim 3, wherein the cylinders are disposed concentrically.

5. A linear capacitance displacement transducer according to claim 1, wherein the first and second cylinders are of substantially the same length.

6. A linear capacitance displacement transducer according to claim 1, wherein the second cylinder is longer than the first cylinder.

7. A linear capacitance displacement transducer according to claim 1, wherein the first and second cylinders are electrically isolated.

8. A linear capacitance displacement transducer according to claim 1, wherein the printed circuit board includes a circuit adapted to perform conversion of a capacitance signal to a displacement value.

9. A linear capacitance displacement transducer according to claim 8, wherein the circuit is adapted to further perform analogue to digital conversion of the capacitance signal.

10. A linear capacitance displacement transducer according to claim 1, wherein at least one of the first, second and third cylinders includes a fluted surface.

11. A linear capacitance displacement transducer according to claim 1, wherein the third cylinder is biased into or from the space in the longitudinal direction.

12. A linear capacitance displacement transducer according to claim 1, wherein the first cylinder is hollow or solid.

13. A linear capacitance displacement transducer according to claim 1, further comprising a fourth cylinder disposed around the second cylindrical capacitor plate for electrically shielding the first and second cylindrical capacitor plates.

14. A reservoir for containing a volume of fluid bound in part by a moveable element, in combination with a linear capacitance displacement transducer for measuring the volume of fluid contained in the reservoir, the displacement transducer comprising:
a fixed structure including first and second capacitor plates; and
a dielectric structure moveable longitudinally within a space between the first and second capacitor plates, wherein the moveable dielectric structure is operatively coupled to the moveable element.

15. A combination according to claim 14, wherein the first capacitor plate is a cylindrical capacitor plate.

16. A combination according to claim 15, wherein the second cylindrical capacitor plate is disposed around the first cylindrical capacitor plate so as to form said space between the first and second cylindrical capacitor plates.

17. A combination according to claim 16, wherein the first and second cylindrical capacitor plates are substantially spatially fixed relative to one another.

18. A combination according to claim 17, wherein the cylinders are disposed coaxially.

19. A combination according to claim 17, wherein the cylinders are right circular cylinders.

20. A combination according to claim 19, wherein the cylinders are disposed concentrically.

21. A combination according to claim 17, wherein the first and second cylinders are of substantially the same length.

22. A combination according to claim 17, wherein the second cylinder is longer than the first cylinder.

23. A combination according to claim 17, wherein the first and second cylinders are electrically isolated.

24. A combination according to claim 23, wherein the first and second cylinders are electrically connected to a printed circuit board.

25. A combination according to claim 24, wherein the printed circuit board includes a circuit adapted to perform conversion of a capacitance signal to a displacement value.

26. A combination according to claim 25, wherein the circuit is adapted to further perform analogue to digital conversion of the capacitance signal.

27. A combination according to claim 17, wherein the first and second cylinders are physically connected to a support structure at adjacent ends thereof.

28. A combination according to claim 27, wherein the support structure is a printed circuit board.

29. A combination according to claim 17, wherein the first cylinder is hollow or solid.

30. A combination according to claim 17, wherein the moveable dielectric structure is a cylinder composed of dielectric material.

31. A combination according to claim 17, wherein at least one of the cylinders includes a fluted surface.

32. A combination according to claim 17, wherein the dielectric structure is biased into or from the space in the longitudinal direction.

33. A combination according to claim 32, wherein the dielectric material is a polymer.

34. A combination according to claim 17, wherein the fixed structure of the linear capacitance displacement transducer is durable and the reservoir and the moveable structure of the linear capacitance displacement transducer are disposable, said moveable element of the reservoir being integrally formed with said moveable structure.

35. A combination according to claim 17, wherein the displacement transducer further includes a cylinder disposed around the second cylindrical capacitor plate for electrically shielding the first and second cylindrical capacitor plates.

36. A combination according to claim 14, wherein the second capacitor plate is a cylindrical capacitor plate.

37. An infusion system for infusion of liquid therapeutic product, including a linear capacitance displacement transducer according to claim 1.

38. An infusion system according to claim 37, further including a pump.

39. An infusion system according to claim 38, wherein the pump comprises a pumping chamber having an inlet valve and an outlet valve, wherein a volume of the pumping chamber is caused to change by operation of an actuator, and wherein the outlet valve has a higher activation pressure than the inlet valve.

40. An infusion system according to claim 38, wherein the pump is disposable.

41. An infusion system for infusion of liquid therapeutic product, including a reservoir in combination with a linear capacitance displacement transducer according to claim 14.

* * * * *